(12) United States Patent
Liprie (10) Patent No.: US 6,629,920 B2
(45) Date of Patent: Oct. 7, 2003

(54) ENERGY FILTERING SYSTEM

(75) Inventor: Sam F. Liprie, Lake Charles, LA (US)

(73) Assignee: Interventional Therapies, Westport, CT (US)

(*) Notice: Subject to any disclaimer, the term of this patent is extended or adjusted under 35 U.S.C. 154(b) by 38 days.

(21) Appl. No.: 09/755,225

(22) Filed: Jan. 5, 2001

(65) Prior Publication Data

US 2003/0149391 A1 Aug. 7, 2003

Related U.S. Application Data

(60) Provisional application No. 60/181,973, filed on Feb. 11, 2000, and provisional application No. 60/175,160, filed on Jan. 7, 2000.

(51) Int. Cl.$^7$ ................................................. A61N 5/00
(52) U.S. Cl. ............................................. 600/1; 600/3
(58) Field of Search ........................................ 600/1–8

(56) References Cited

U.S. PATENT DOCUMENTS

| | | |
|---|---|---|
| 4,819,618 A | 4/1989 | Liprie |
| 4,976,680 A | 12/1990 | Hayman et al. |
| 5,059,166 A | 10/1991 | Fischell et al. |
| 5,084,002 A | 1/1992 | Liprie |
| 5,141,487 A | 8/1992 | Liprie |
| 5,183,455 A | 2/1993 | Hayman et al. |
| 5,199,939 A | 4/1993 | Dake et al. |
| 5,213,561 A | 5/1993 | Weinstein et al. |
| 5,267,960 A | 12/1993 | Hayman et al. |
| 5,282,781 A | 2/1994 | Liprie |
| 5,302,168 A | 4/1994 | Hess |
| 5,322,499 A | 6/1994 | Liprie |
| 5,395,300 A | 3/1995 | Liprie |
| 5,503,613 A | 4/1996 | Weinberger |
| 5,503,614 A | 4/1996 | Liprie |
| 5,540,659 A | 7/1996 | Teirstein |
| 5,556,389 A | 9/1996 | Liprie |
| 5,575,749 A | 11/1996 | Liprie |
| 5,618,266 A | 4/1997 | Liprie |
| 5,624,372 A | 4/1997 | Liprie |
| 5,643,171 A | 7/1997 | Bradshaw et al. |
| 5,807,231 A | 9/1998 | Liprie |
| 5,816,999 A | 10/1998 | Bischoff et al. |
| 5,833,593 A | 11/1998 | Liprie |
| 5,840,064 A | 11/1998 | Liprie |
| 5,857,956 A | 1/1999 | Liprie |
| 5,863,284 A | 1/1999 | Klein |
| 5,882,291 A | 3/1999 | Bradshaw et al. |
| 5,910,101 A | 6/1999 | Andrews et al. |
| 5,947,924 A | 9/1999 | Liprie |
| 6,059,714 A | 5/2000 | Armini et al. |
| 6,196,963 B1 | 3/2001 | Williams |

OTHER PUBLICATIONS

Becker et al., Radiofrequency Balloon Angioplasty, Rationale and Proof of Principle, Investigative Radiology, (Nov. 1988), p. 810.

Bottcher et al., Endovascular Radiation –A New Method to Avoid Recurrent Stenosis After Stent Implantation in Peripheral Arteries: Technique and Preliminary Results, International Journal of Radiation Oncology, Biology and Physics, vol. 29, No. 1, pp. 183–186 (1994).

*Primary Examiner*—J. Casimer Jacyna
(74) *Attorney, Agent, or Firm*—Cantor Colburn LLP (57) ABSTRACT

An energy filtering system including an energy filtering material provided between a radioactive material and a treatment target such that radioactive energy is filtered. In a preferred embodiment, the filtering material is provided as a thin-walled layer, such as a micro-foil, mesh, helically wound spring, film, coating or stackable right-angle disks, among others, at one or more locations between the radioactive source and a treatment target, to filter the radiation energy during treatment. The filtering material may be a high-density material, such as platinum, applied or incorporated in a supporting structure between the radioactive material and the treatment target. The supporting structure may include a catheter having a treatment end, a source wire movable within the catheter, a stent or indeed, any structure positionable between a source of radiation and a treatment site.

48 Claims, 8 Drawing Sheets

ENERGY FILTERING SYSTEM

CROSS REFERENCE TO RELATED APPLICATIONS

This application claims the benefit of an earlier filing date from U.S. Provisional Application Serial No. 60/175,160, filed on Jan. 7, 2000 and 60/181,973 filed on Feb. 11, 2000 which is fully incorporated herein by reference.

TECHNICAL FIELD

The present invention relates to catheters and/or source wires and/or radioactive stents for treatment of a stenosis within a bodily conduit. More particularly, the present invention relates to a catheter and/or source wire and/or radioactive stents further comprising an energy filter.

BACKGROUND OF THE INVENTION

Percutaneous Angioplasty ("PTA") is presently an effective treatment for the severely occluded coronary artery. A significant problem with angioplasty, however, is the reoccurrence of the occlusion. Post re-occlusion often necessitates additional PTA. Becker et al., Radiofrequency Balloon Angioplasty, Rationale and Proof of Principle, *Investigative Radiology*, (November 1988), p. 810.

It has previously been suggested that radiation applied in appropriate dosages retards smooth muscle proliferation that is characteristic of restenosis. Various techniques have been developed to treat restenosis in bodily conduits using catheters and radioactive materials. One such technique includes introducing a catheter to the treatment site, positioning radioactive material inside the catheter for a specified period of time, and removing the radioactive material and catheter from the conduit after the allocated time period. Bottcher et al., *Endovascular Radiation —A New Method to Avoid Recurrent Stenosis After Stent Implantation in Peripheral Arteries: Technique and Preliminary Results, International Journal of Radiation Oncology, Biology and Physics*, Vol. 29, No. 1, Pages 183–186 (1994).

U.S. Pat. No. 5,059,166 to Fischell et al. discloses the positioning of radioactive intra-arterial stents at a treatment site for the reduction of restenosis in the vasculature, wherein the radioactive material is an alpha, Beta or Gamma emitter.

U.S. Pat. No. 5,302,168 to Hess describes a method and apparatus for reducing restenosis wherein radioactive material is included within the distal end of a treatment catheter, on the exterior of a catheter or included on an expandable stent positioned on the exterior of a catheter for radiation treatment of the stenosis. The patent to Hess further describes an embodiment wherein a selective energy shield is positioned over the radioactive material that is operatively connected to the catheter such that during positioning of the catheter, the shield, when positioned over the radioactive material, blocks the emitted radiation until needed.

U.S. Pat. Nos. 5,840,064 and 5,947,924 to Liprie, the disclosures of which are herein incorporated by reference, describe a method and apparatus for treating a stenosis including advancement of a source wire through a treatment lumen in a catheter equipped with dilation and/or centering balloons for controlled irradiation of the stenosed region. U.S. Pat. Nos. 5,503,614 and 5,857,956 to Liprie, the disclosures of which are herein incorporated by reference, disclose flexible source wires for radiation treatment of a stenosed site wherein the source wire includes an encapsulated radioactive source provided in a housing tube, and a flexible backbone inserted within the housing tube.

When treating restenosis or other diseases inside a bodily conduit, such as a blood vessel, with a radioactive source, often it is very important to precisely control how that emitted radiation affects the various exposed vessel tissues. It is known that ineffective treatment of vessel walls will generally occur where a radiation source rests near a vessel wall rather than in a position offset from the vessel wall. The art further recognizes that uneven irradiation of tissue is particularly problematic within the tortuous regions of the vasculature. Thus the art emphasizes the need to effectively center, or at least offset, the radioactive source within the vessel to prevent ineffective radiation delivery to the target site.

Depending on the location of the diseased area, often the radioactive source must stay in the blood vessel several minutes (5–20 minutes, or longer) to ensure that the proper radiation dose is delivered to the treatment site. Excessive radiation can promote hyperplasia at the target site rather than reduce smooth muscle proliferation. Accordingly, the exposure time is calculated with regard to the portion(s) of the vessel wall receiving the greatest dose. If the catheter design does not provide for catheter offset, the difference in tissue adsorptions can be profound, and an ineffective dose will be delivered to the remainder of the treatment site. For example, the target site away from the radioactive source can adsorb something on the order of 15 Gray (Gy) while the intima (i.e., the portion of the blood vessel wall proximal to the radioactive source) adsorbs 100 Gy or more.

Centering provides some measure of control, wherein the source wire is positioned as far away from the inner vessel wall as possible. Damaging surface activity/exposure to portions of the vessel wall is thus reduced while the proper radiation dose is delivered to the treatment site. One method of distancing the source from the vessel wall is described by U.S. Pat. No. 5,863,284 to Klein and U.S. Pat. No. 5,910,101 to Andrews et al. These patents describe a technique whereby a balloon is inflated on the catheter housing to center the radioactive material. The patents teach the importance of centering the radioactive source within the bodily conduit at the stenosed site, particularly under circumstances where treatment occurs within the tortuous regions of the vasculature.

Another method for positioning the source away from the inner vessel wall includes use of a thick walled catheter, wherein the thickness of the catheter wall is such that the catheter's overall profile approximates that of an inflated balloon catheter. The thick walled catheter embodiment similarly recognizes the importance of offsetting the radioactive source from a vessel wall such that portions of the vessel intima do not excessively adsorb radiation.

Balloons and thick walled catheters, each useable to offset or center a source, provide limitations that compromise treatment. Centering balloons must be inflated during the entire treatment phase. The area occupied by the inflated balloon inside the lumen greatly reduces blood flow. Although there are many different shapes of balloons, the volume of the inflated balloon combined with the narrow lumen opening and the irregular plaque shape, all add up to constrict or greatly diminish blood flow, which can be problematic for the patients. Both the inflated balloon and the thick walled catheter occlude the vessel opening either to totally block or greatly limit blood flow during treatment. Since treatments can last 5–20 minutes or longer, it is often necessary to remove the radioactive material and devices so greater perfusion can take place. Once blood flow of the patient is restored, the devices are repositioned and the treatment is resumed where it left off. In some patients due to the decreased perfusion, the treatment is interrupted several times before the total dose of radiation is delivered.

Use of a balloon to center or offset a catheter adds complexity to the catheter and increases the complexity of the treatment procedure with regard to overall procedure duration, taking into account the need for interruption and resumption of treatment to allow perfusion. Increased device complexity and operation time translates disadvantageously to increased overall cost of the medical procedure. What is needed in the art is an effective method for delivering an even radiation dose to the treatment site without the need for a catheter centering balloon.

Another limitation of current methods and devices includes the inaccessibility of the smaller vessels, where the openings are too narrow for the thick wall catheter and/or inflated balloon catheter to fit. A partially-inflated balloon catheter or a thinner wall catheter may allow access to these smaller vessels, but does not solve the problem of off-center irradiation of the inner vessel wall. Clinically, treatment of the patient would either not be possible or not be practicably effective.

Accordingly, there remains a need in the art for a catheter system that provides an even radiation dose to a treatment site, including treatment sites located in the smaller blood vessels, without overly occluding blood flow.

SUMMARY OF THE INVENTION

The above discussed and other drawbacks and deficiencies of the prior art are overcome or alleviated by the energy filtering system of the present invention. The energy filtering system includes an energy filtering material provided between a radioactive material and a treatment target such that radioactive energy is filtered. In a preferred embodiment, the filtering material is provided as a thin-walled layer, such as a micro-foil, mesh, helically wound spring, film, coating or stackable right-angle disks, among others, at one or more locations between the radioactive source and a treatment target, to filter the radiation energy during treatment.

The filtering material may be a high-density material, such as platinum, applied or incorporated in a supporting structure between the radioactive material and the treatment target. The supporting structure may include a catheter having a treatment end, a source wire movable within the catheter or a combination of both. Alternatively, the energy filter may be affixed to a radioactive stent disposed at the treatment site.

In one embodiment, the energy filter is disposed at the distal end of a catheter containing a radioactive source. The filter substantially surrounds the source, selectively passing energy from the source to the target area needing treatment.

In another embodiment, the energy filter is disposed at the distal end of a source wire movable within a catheter. The source wire contains a radioactive source. The filter substantially surrounds the source, selectively passing energy from the source to the target area needing treatment.

In another embodiment, the energy filter is disposed in both the treatment end of a catheter and at the distal end of a source wire movable within the catheter. The energy passes from the distal end of the source wire through a first filter material on the source wire and then through a second filter material disposed on the catheter, thereby selectively passing energy from the source to the target area needing treatment.

In another embodiment, the energy filtering material is disposed on a stent containing a radioactive source. The filter material is disposed between the radiation source and the treatment site, thereby selectively passing energy from the source to the target area needing treatment.

The above description and other features and advantages of the present invention will be appreciated and understood by those skilled in the art from the following detailed description, drawings, and appended claims.

BRIEF DESCRIPTION OF THE DRAWINGS

Referring now to the drawings wherein like elements are numbered alike in the several FIGURES.

DESCRIPTION OF THE PREFERRED EMBODIMENT

Figure 1:
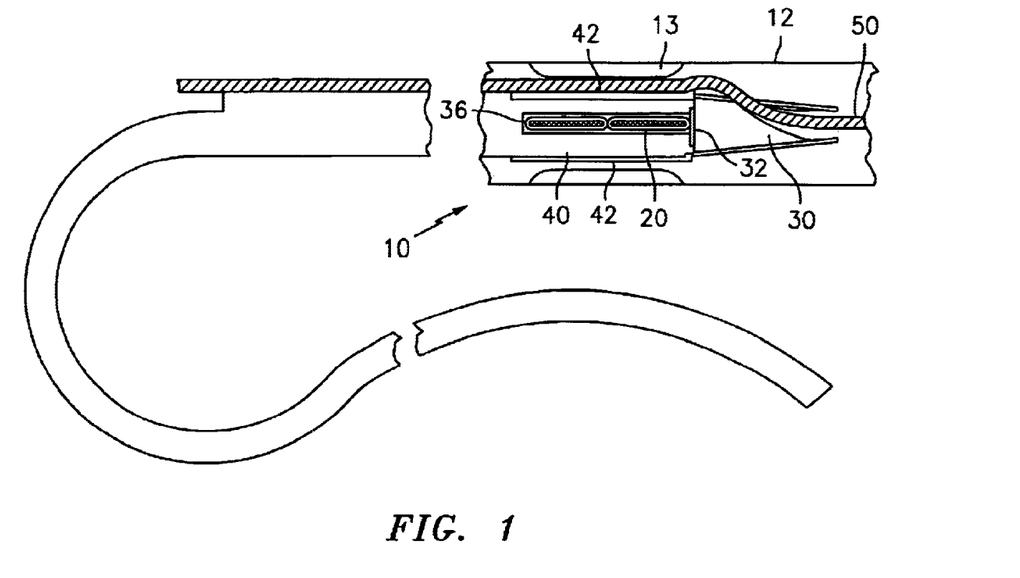
FIG. 1 is a cross-sectional side view of a catheter containing an energy filter for selectively passing radiation from a radioactive source to a target area.

Referring now to FIG. 1, an energy filter 42 for selectively passing energy from a radioactive-source to a target area needing treatment is generally shown at 10. Catheter 30 is shown inserted over a guide wire 50 such that radioactive material 20 is positioned at a stenosed area 13 of vessel 12. Radioactive material 20 is positioned within a cavity 36 of the catheter and is sealed at distal end 32. Cavity 36 is dimensioned to contain radioactive material 20. Energy filtering material 42 is included external to catheter wall 40.

Figure 2:
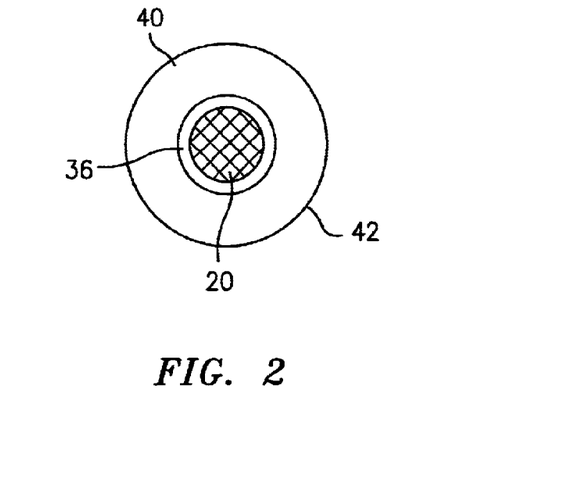
FIG. 2 is a frontal view of the catheter of FIG. 1 showing the filter material exterior to the catheter wall.

Turning now to FIG. 2, a longitudinal cross section of catheter 30 including radioactive material 20 within catheter cavity 36 is illustrated. Energy filtering material 42 is included external to catheter wall 40 such that the filter material 42 is generally located between radioactive material 20 and the target area needing treatment.

Figure 3:
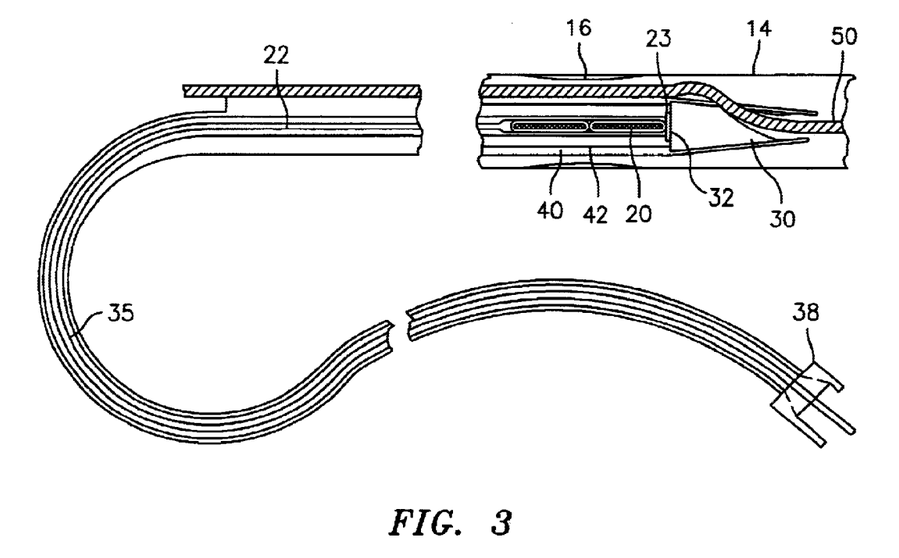
FIG. 3 is cross-sectional side view of another catheter containing an energy filter for selectively passing radiation from a radioactive source to a target area.
Figure 4:
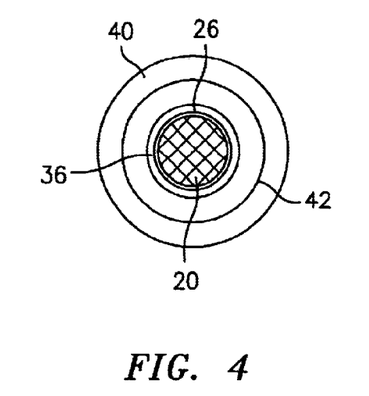
FIG. 4 is a frontal view of the catheter of FIG. 3, showing the filter material within the catheter wall.
Figure 5:
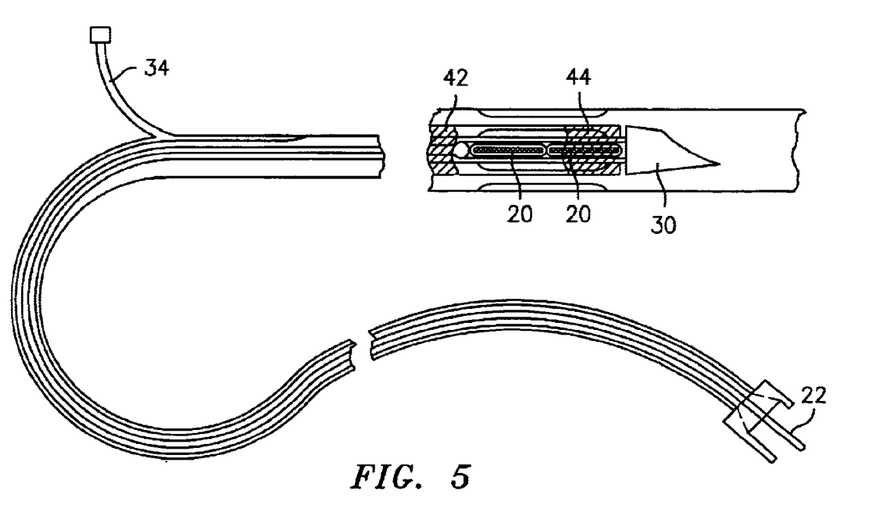
FIG. 5 is a cross-sectional side view of a balloon catheter surrounded by a selective energy filtering shield for filtering radiation from a radioactive source provided in a source wire.

Now referring to FIGS. 3 and 4, a second embodiment of the present invention is generally illustrated. Energy filter 42 is shown within catheter wall 40. Source wire 22 is shown inserted through conduit 35 such that radioactive material 20 is positioned within catheter 30 adjacent to the target area needing treatment (stenosed area) 16 of smaller vessel 14. End 38 of conduit 35 provides attachment to an extension tube (not shown) or afterloader apparatus (not shown). Source wire 22 encloses radioactive material 20 at a distal portion 23 of source wire 22. Catheter conduit 35 includes a blind seal at distal end 32. FIG. 5 is a cross sectional view of the catheter of FIG. 4, showing energy filtering material 42 within catheter wall 40.

Referring now to FIG. 5, another embodiment of the instant invention is shown. Energy filter 42 is disposed on catheter 30 including a balloon 44. Radioactive material 20 is incorporated in source wire 22 (as in the embodiment of FIG. 3). Alternatively, radioactive material could be incorporated within catheter 30 (as in the embodiment of FIG. 1). Balloon 44 may optionally include centering and/or perfusion structures as is well known to one of ordinary skill in the art. Balloon 44 is positioned adjacent to the target area needing treatment. Port 34 provides inflation to balloon 44 when in position.

Figure 6:
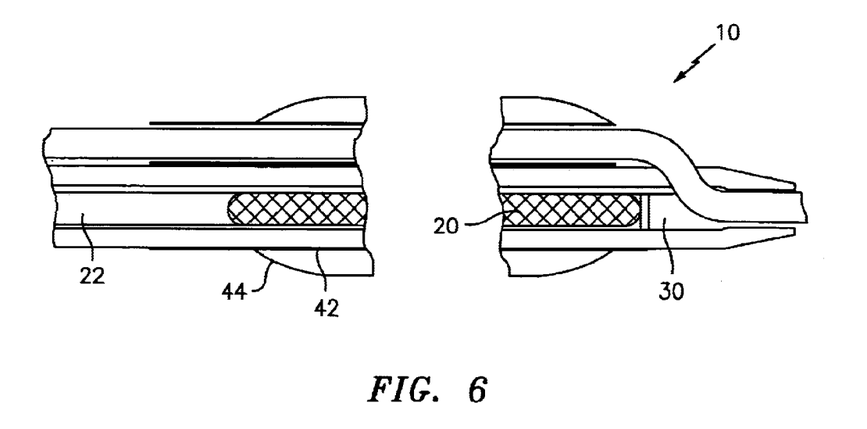
FIG. 6 is a cross-sectional side view of another balloon catheter containing filtering material for selectively passing radiation from a radioactive source to a target area.

Turning now to FIG. 6, another embodiment of the present invention is shown. Energy filter 42 is disposed on the catheter wall 40 of catheter 30. Radioactive material 20 is incorporated in a source wire 22. Alternatively, radioactive material could be incorporated within catheter 30. Balloon 44 may optionally include centering and/or perfusion structures as is well known to one of ordinary skill in the art.

Figure 7:
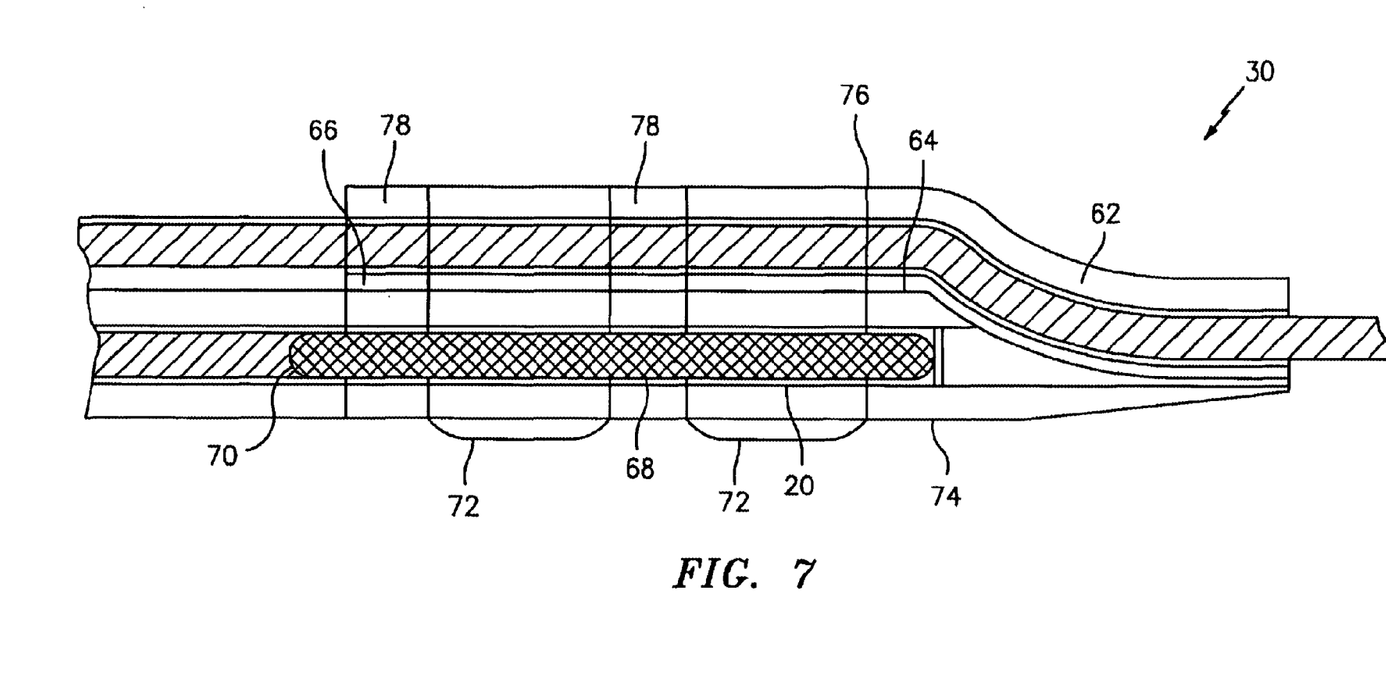
FIG. 7 is a cross-sectional side view of another balloon catheter containing filtering material for selectively passing radiation from a radioactive source to a target area.

Turning now to FIG. 7, an alternate embodiment of the catheter of FIG. 6 is shown, wherein a guidewire channel 62 extends from a distal end of the catheter 30 along a first shaft portion 64 of the catheter 30 and terminates at a point 66 adjacent the proper position for a radioactive source 20. Preferably, the guidewire channel 62 terminates between the midpoint 68 and the proximal end 70 (toward the physician) of the radioactive source position. It is particularly preferred that the guidewire channel terminates between 10 and 15 percent of the core length short of the proximal end 70 of the radioactive source 20.

Referring still to FIG. 7, the catheter 30 preferably includes a balloon 72, in fluid communication with an inflation lumen (not shown), disposed at least partially along a second shaft portion 74 of the catheter. While the expanded radius of the balloon may be greater than the preferred range, the balloon 72 preferably has a maximum expanded radius of 0.2 millimeters beyond the catheter shaft. The inflated balloon 72, in combination with the guidewire channel 62, provides an even, somewhat circular profile near the treatment area. As in FIG. 6, the energy filter 42 is disposed on or within the catheter wall 40 of the catheter 30.

The catheter 30 of FIG. 7 is preferably manufactured by gluing or otherwise attaching a separate guidewire channel 62 to the catheter shaft. The preferred balloon 72 is sealed around the shaft, preferably up to the sides of the guidewire channel 62. A laminate 76 and/or lamination bands 78, are then placed around the guidewire channel 62 and balloon 72 such that they are secured to the catheter shaft.

Figure 8:
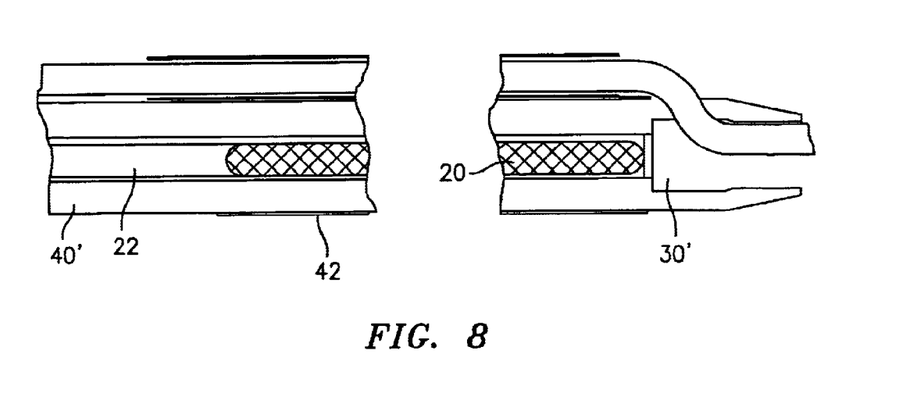
FIG. 8 is a cross sectional side view of a thick walled catheter containing an energy filter for selectively passing radiation from a radioactive source to a target area.

Turning now to FIG. 8, another embodiment of the present invention is illustrated. Energy filter 42 is provided on wall 40' of thick walled catheter 30'. Alternately, energy filter 42 may be provided within wall 40' of catheter 30' as is shown in FIG. 3. Radioactive material 20 is incorporated in a source wire 22. Alternately, radioactive material could be incorporated within catheter 30'.

Figure 9:
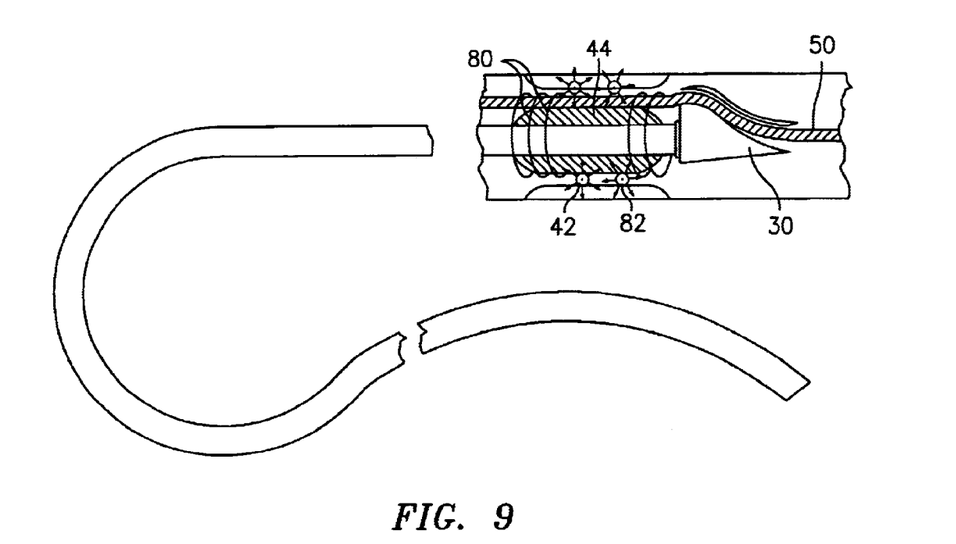
FIG. 9 is a cross-sectional side view of a radioactive stent further including a filtering material between the radioactive stent material and the target site.

Turning now to FIG. 9, another embodiment of the present invention is illustrated. Energy filter 42 is disposed on radioactive stent 80 shown partially deployed by balloon 44. In this embodiment, catheter 30 is inserted over guidewire 50. Stent 80 is positioned over balloon 44 prior to deployment at the target area. Upon positioning catheter 30 such that balloon 44 and stent 80 are adjacent to the target area needing treatment, balloon 44 is inflated, thereby expanding and deploying stent 80. Energy filter 42 selectively filters radiation source 20 disposed on stent 80, to selective pass energy to the target area.

Referring again to FIG. 9, a cross sectional view of stent 80 is also shown. Filtering material 82 is external to radioactive material, which is provided as a core or as part of stent structure.

Figure 10:
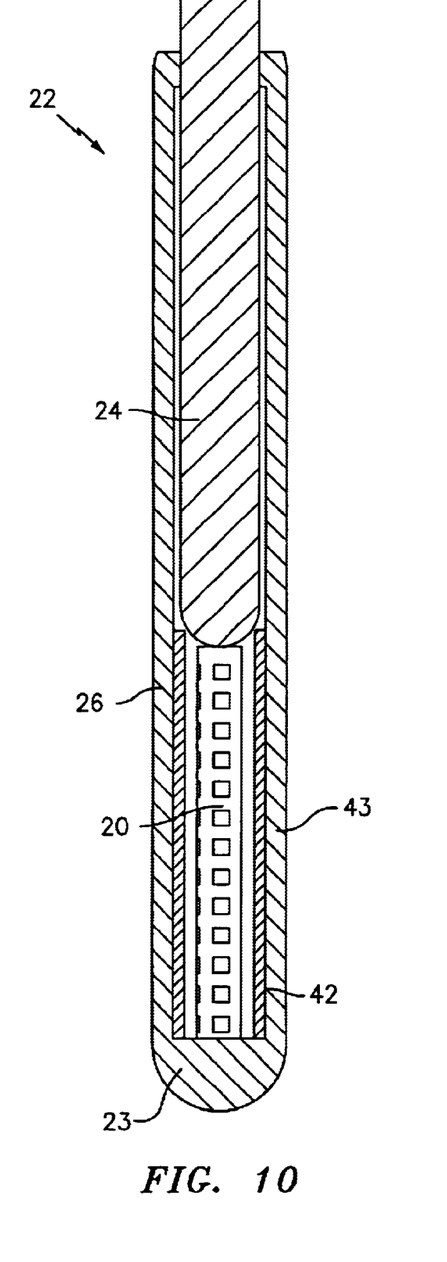
FIG. 10 is a cross-sectional side view of a source wire further comprising an energy filtering material as a layer inside the source wire housing.
Figure 11:
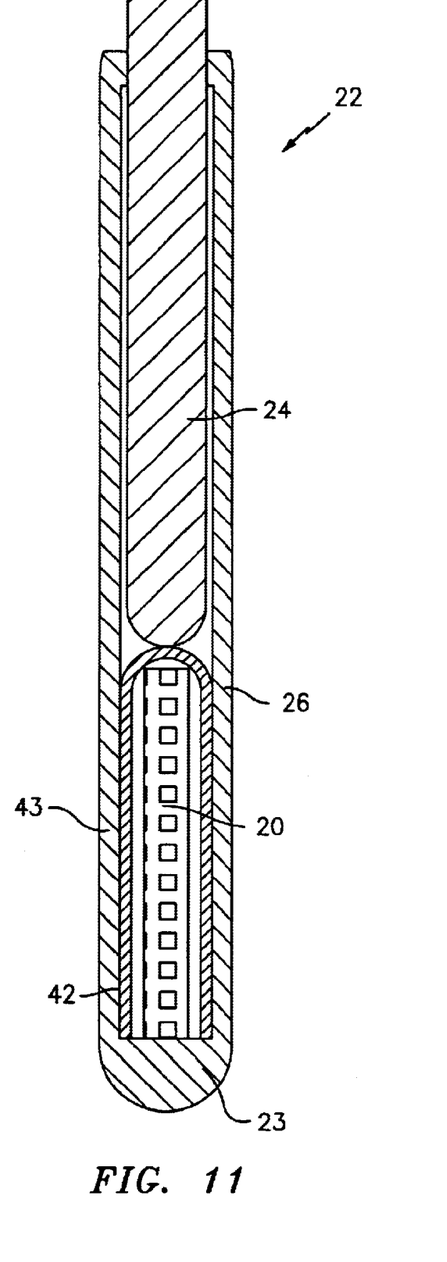
FIG. 11 is a cross-sectional side view of a source wire further comprising and energy filtering material inside the source wire housing and substantially surrounding the radioactive material.

Referring to FIG. 10 source wire 22 is further illustrated. Radioactive material 20 is provided within housing tube 26. Energy filtering material 42 is disposed on inner wall 43 of housing tube 26. Flexible backbone 24 is inserted into housing tube 26. Alternatively, as shown in FIG. 11, energy filtering material 42 may further be disposed between flexible backbone wire 24 and radioactive material 20.

Figure 12:
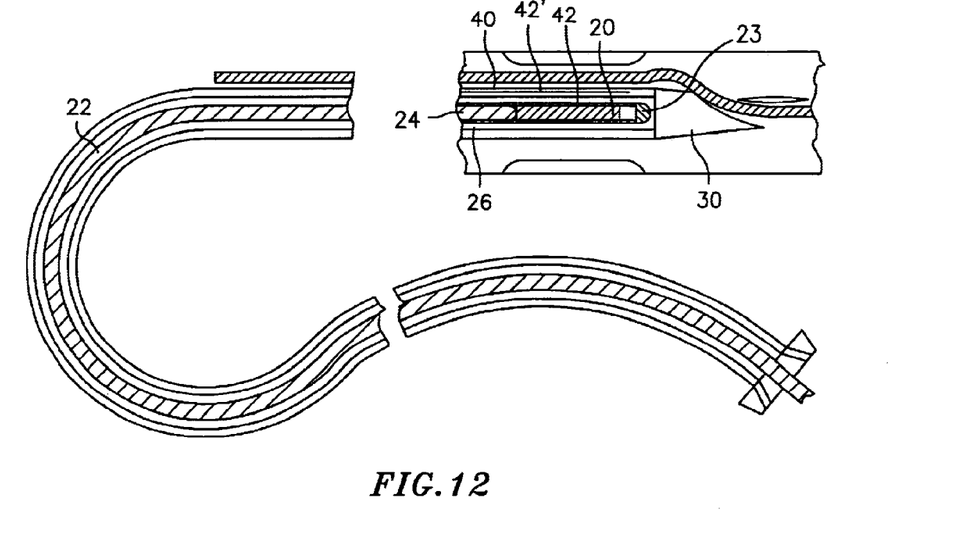
FIG. 12 is a cross-sectional side view of a catheter including an energy filter and a source wire having another energy filter, the two filters substantially surrounding a radioactive source, such that radiation is filtered by either or both of the energy filtering material on the source wire and the energy filtering material within the catheter.

Referring to FIG. 12, another embodiment of the present invention is generally shown. First energy filter 42 is disposed on distal end 23 of source wire 22. (FIG. 12 shows an alternative to the embodiment shown in FIG. 10. In FIG. 12, filtering material 42 is disposed on the exterior wall of housing tube 26). Second energy filter 42' is disposed within wall 40 of catheter 30. Thus, radioactive source 20 is selectively filtered by both or either of energy filter 42 and energy filter 42' prior to irradiating the target area needing treatment.

Figure 13:
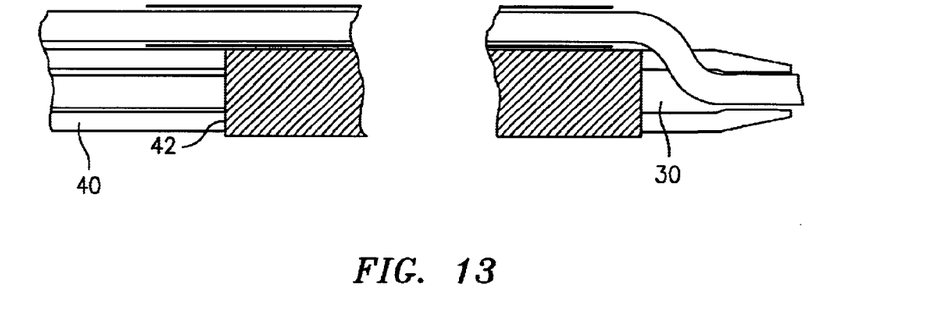
FIG. 13 is a cross-sectional side view of a catheter including an energy filter provided as a spring or helical coil.

Turning now to FIG. 13, another embodiment of the present invention is generally shown. Energy filter 42 is provided as a spring or helical coil on catheter 30. Alternately, spring or coil filter material 42 may be provided 30 within catheter wall 40 as is shown in FIG. 3, exterior to catheter balloons as is shown by FIG. 5, within a source wire as is shown by FIGS. 10 and 11 or exterior to a source wire as is shown by FIG. 12. The spring material 42 may have a circular cross-section or other appropriate cross-section, including a flat or ribbon-like configuration.

Figure 14:
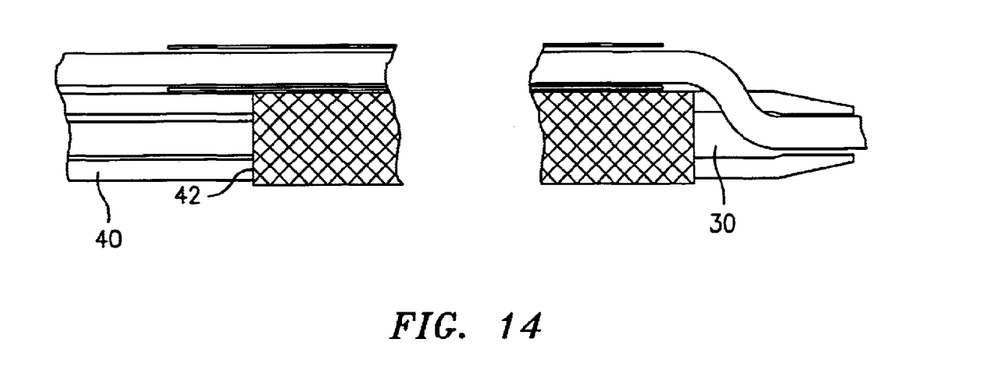
FIG. 14 is a cross-sectional side view of a catheter including an energy filter provided as a mesh material.

Turning now to FIG. 14, another embodiment of the present invention is generally shown. Energy filter 42 is provided as a mesh on catheter 30. Alternately, mesh filter material 42 may be provided within catheter wall 40 as is shown in FIG. 3, exterior to catheter balloons as is shown by FIG. 5 or within a source wire as is shown by FIGS. 10 and 11 or exterior to a source wire as is shown by FIG. 12.

Figure 15:
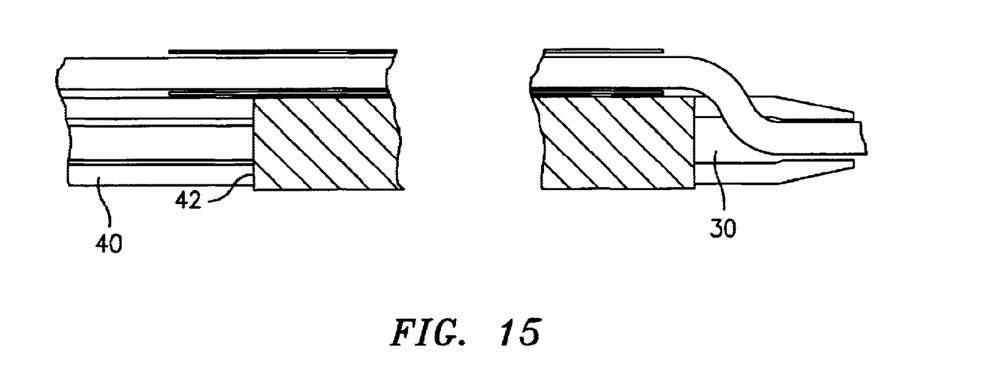
FIG. 15 is a cross-sectional side view of a catheter including an energy filter provided as a series of stackable right angle disks.

Turning now to FIG. 15, another embodiment of the present invention is generally shown. Energy filter 42 is provided as a series of segmented disks (such as stackable right angle disks) on catheter wall 30, which result in a flexible housing. Alternately, disk filter material 42 may be provided within catheter wall 40 as is shown in FIG. 3, exterior to catheter balloons as is shown by FIG. 5 or within a source wire as is shown by FIGS. 10 and 11 or exterior to a source wire as is shown by FIG. 12.

Thus, the present invention describes an apparatus and method for treating an occlusion or constriction, such as a stenosis in a blood vessel or other conduit in the body. The instant invention may also be used as system and method for treating other diseases such as but not limited to, a tumor or cancerous area existing adjacent a conduit or duct in the body, where selectively filtering the radiation energy allows for a more uniform application of the radiation to the treatment area.

As is known to those of ordinary skill in the art, Alpha, Beta, Gamma and X-ray radiation penetrate the target and surrounding treatment area to differing degrees. Certain low energy sources, such as Beta radiation, have a relatively limited range of effective use. Thus, when an unfiltered source is adjacent to a treatment site, areas proximal to the source receive both the high and the low energy radiation, while areas more distal to the radiation source receive only the high energy radiation. This in essence causes an uneven distribution of the radiant energy, particularly when the source is not offset or centered. In accordance with the instant invention, an energy filter, such a platinum foil which can filter low energy radiation while allowing high energy radiation to pass, is particularly preferred in vascular applications having treatment targets greater than about 1 to 1.5 mm from the radioactive material.

Beta sources provide a good example. Most Beta sources emit electrons that rapidly dissipate to insignificant radiation levels at distances of above about 1 to 1.5 mm. Because exposure falls off substantially after about 1 to 1.5 mm, the emission of Beta radiation generally promotes surface activity primarily in the intima layers of the vessel wall adjacent the radioactive source. Where portions of the treatment site extend beyond, uneven irradiation of the treatment site occurs.

Because, high energy radiation (most Gamma sources provide such high energy radiation) penetrates further through tissue, the need for centering a radioactive source within a vessel is eliminated with the filtering material of the present invention. Therefore, a bumping (for providing offset) balloon, centering balloon or thick walled catheter (above about 0.020 inches wall thickness) is not necessary.

The present invention advantageously provides a thin filter for filtering such low energy radiation while allowing for smallest profile and greatest flexibility possible for the catheter. This small profile allows the catheter to move from side to side within the vessel (the offset/centering requirement is obviated by the filter of the present invention), providing the maximum amount of perfusion possible during treatment. This modification (smaller profile) is possible because the filter of the present invention protects the inner vessel wall from adsorbing excessive irradiation.

Where a balloon is still desired, the filtering material guarantees that the balloon does not have to be inflated to as large a diameter as is otherwise required, as the need for offset is alleviated. Similarly, where a heavy wall catheter is still desired, the filtering material guarantees that the catheter may have a thinner wall than would otherwise be required. Therefore, the filtering material (preferably thin and flexible in nature) provides the thinnest profile catheter system possible, while allowing therapy in areas that currently cannot be treated due to the narrow lumen opening inside the vessel. Similarly, the filtering material of the present invention allows treatment in areas where the decreased perfusion from larger devices would endanger the patient.

Filtering materials may be incorporated at any convenient location or locations between the radioactive source and the vessel intima. For example, as indicated by FIG. 12, filtering materials may be included within the catheter wall and within the sourcewire. Indeed, filtering materials may be disposed on or within any combination of supporting structures in any convenient geometry. Filtering material geometries or combinations of geometries contemplated by the present invention include, but are not limited to, microfoils, mesh, coatings, films, helically wound springs and stackable right angled discs, among others.

Preferred filtering materials include high-density materials, such as platinum among others, applied or incorporated at approximately 0.001 inches of wall thickness (or less). Although platinum is a particularly preferred filtering material, since its density is 21.45 g/cm$^{-3}$ and since it is highly malleable, other high-density materials are useful in the embodiment. The type of filtering may be varied by carefully selecting the isotope of the high-density material used. Where suitable, mixtures of one or more high-density materials may be used as a filtering material. Similarly, one or more isotopes of the same or of different high-density materials may be used. It is also preferred that a lamination or other sealing layer be applied over the filtering material to assure that it stays bound to the supporting structure and does not move.

Preferred filtering materials are flexible, such that they will not degrade the trackability of the catheter and/or source wire, when such structures are used to support filtering materials. The particularly preferred material and thickness parameters described above provide exceptional filtering performance while retaining good catheter/source wire trackability. Accordingly, the preferred embodiment should be adhered to where practicable, it being realized that other materials and greater thicknesses may be selected to target the particular type of energy to be filtered and the particular requirements of the various minimally invasive medical procedures contemplated by the present invention.

Various radioactive sources may be used, provided as a core, as one or more spherical or cylindrical sources, or indeed, in any convenient geometrical form. As discussed above, the radioactive material (20) may be provided on a variety of supporting structures, including a stent, catheter and/or source wire, and in any convenient location (e.g., cavity, wall, exterior). Exemplary radioactive sources include Ir-192, P-32, Co-57, Co-60, Cs-137, Sr-89, Sr-90, Y-90, Au-198, I-125, Pd-103, Se-75 and Ru-106, among others.

Other preferred materials for the present catheter include radiated polyethylene, Pebax or Nylon, among others, for the balloon material. Preferred materials for the guidewire channel and the source wire lumen include high density polyethylene, among others. Preferred material for the catheter shaft includes polyethylene, Pebax, Nylon or Hytrel, among others.

In the preferred practice of present invention, a radiopaque guide wire is inserted into the body through a small incision and is then introduced into a blood vessel or similar conduit. Once in place, a catheter having an energy filter (covering at least a portion of the area where the radioactive material will preside) is threaded over the guide wire and advanced to the location of treatment. Marker bands are preferably mounted on the catheter showing the area where the radioactive material will be positioned during the treatment phase, ensuring that the treatment zone of the catheter (protected by the filtering material) will be visible under fluoroscopy. Radioactive material is then preferably maneuvered through the inside of the catheter (though the catheter itself may contain radioactive materials in the treatment area) to the treatment location. The radioactive material and catheter are held in place for a specified time period, after which time they are removed from the body. The guide wire may then be left in place temporarily to give access to the treatment site, if necessary, and then removed once it is no longer needed.

A further advantage of incorporation of the energy filtering material into the catheter, source wire, stent, etc., is that the preferred energy filtering materials are radiopaque under fluoroscopy. Accordingly, such materials may be strategically included on or within the supporting structures with the added advantage of marking the positions of the energy filtering materials. Clinical application particularly prefers incorporation of the energy filtering material, primarily within the source wire to mark under fluoroscopy the filtered treatment zone positions of the source wire within the catheter.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A device for filtering radiant energy at a treatment site within the mamalian body, comprising:
    a source of radiation positionable at a treatment site; and
    a filtering material provided at least partially around the source to selectively filter radiation energy transmitted to the treatment site.

2. The device of claim 1, further comprising a supporting structure provided between the source and the treatment site, and wherein the filtering material is provided on or within the supporting structure.

3. The device of claim 2, wherein the supporting structure is a catheter.

4. The device of claim 3, wherein the filtering material is disposed within the wall of the catheter.

5. The device of claim 3, wherein the filtering material is disposed on the exterior of the catheter body.

6. The device of claim 3, wherein the catheter is a balloon catheter and wherein the filtering material is disposed exterior on or within the balloon.

7. The device of claim 3, wherein the catheter further includes a guidewire channel on or within a first catheter shaft portion having proximal and distal exit ports.

8. The device of claim 7, wherein the proximal exit port is positioned distally of the proximal end of the operative position of a radioactive core.

9. The device of claim 8, wherein the proximal exit port is positioned proximally of the midpoint of the operative position of a radioactive core and distally of the proximal end of the operative position of a radioactive core.

10. The device of claim 9, wherein the proximal exit port is positioned above about 10 percent distally of the operative position of a radioactive core.

11. The device of claims 7–10, wherein the catheter further includes a balloon secured to a second catheter shaft portion.

12. The device of claim 2, wherein the supporting structure is provided external to a catheter.

13. The device of claim 12, wherein the catheter is a balloon catheter and the supporting structure is a substantially cylindrical body provided around the balloon.

14. The device of claim 2, wherein the supporting structure is a thick-walled catheter.

15. The device of claim 2, wherein the supporting structure is a stent.

16. The device of claim 2, wherein the filtering material is provided on the supporting structure at a thickness of about 0.001 inches or less.

17. The device of claim 2, wherein the supporting structure is a source wire.

18. The device of claim 17, wherein the filtering material is disposed on the exterior of the source wire.

19. The device of claim 18, further comprising a laminant provided over the filtering material to prevent slippage or damage to the filtering material.

20. The device of claim 17, wherein the filtering material is provided on the interior surface of the source wire incident to the source.

21. The device of claim 20, wherein the filtering material substantially surrounds the source.

22. The device of claim 1, further comprising first and second supporting structures provided between the source and the treatment site, and wherein the filtering material is provided on or within the first and second supporting structures.

23. The device of claim 1, wherein the first supporting structure is a source wire and wherein the second supporting structure is a catheter.

24. The device of claim 1, wherein the filtering material comprises a spring or a helically wound coil.

25. The device of claim 1, wherein the filtering material comprises a mesh.

26. The device of claim 1, wherein the filtering material comprises a series of stackable right angle disks.

27. The device of claim 1, wherein the filtering material is a high density material.

28. The device of claim 27, wherein the filtering material is platinum.

29. The device of claim 27, wherein the filtering material is sufficiently malleable to track through the vasculature.

30. The device of claim 1, wherein the source is Ir-192, P-32, Co-57, Co-60, Cs-137, Sr-89, Sr-90, Y-90, Au-198, I-125, Pd-103, Se-75 or Ru-106.

31. The device of claim 1, wherein the source is sufficiently radiopaque such that it will be visible with fluoroscopy.

32. A device for filtering radiant energy at a treatment site within the mamalian body, comprising:
    a source of radiation positionable at a treatment site;
    a filtering material provided at least partially around the source to selectively filter radiation energy transmitted to the treatment site, the filtering material provided on or within a catheter supporting structure provided between the source and the treatment site;
    a guidewire channel on a first catheter shaft portion, the guidewire channel having proximal and distal exit ports, wherein the proximal exit port is positioned distally of the proximal end of the operative position of a radioactive core; and
    a balloon secured to a second catheter shaft portion.

33. The device of claim 32, wherein first and second catheter shaft portions share at least one common point on the longitudinal axis of the catheter shaft.

34. The device of claim 32, wherein the guidewire channel and the balloon are further secured to the catheter shaft by a laminate.

35. The device of claim 34, wherein the guidewire channel and the balloon are secured to the catheter shaft by one or more lamination bands encircling the catheter shaft about the longitudinal axis.

36. The device of claim 32, wherein the proximal exit port is positioned proximally of the midpoint of the operative position of a radioactive core and distally of the proximal end of the operative position of a radioactive core.

37. The device of claim 36, wherein the proximal exit port is positioned above about 10 percent distally of the operative position of a radioactive core.

38. The device of claim 21, wherein the filtering material has a density of above about 20 grams per cubic centimeter.

39. A method of filtering radiation for treatment of a target within the mammalian body, comprising:

emitting radiation from a source positionable at a treatment site; and selectively filtering the radiation by interposing a filtering material between the source and the treatment site.

40. The method of claim 39, wherein the filtering material is provided on a supporting structure.

41. The method of claim 40, wherein the filtering material is a catheter.

42. The method of claim 40, wherein the filtering material is a source wire.

43. The method of claim 40, wherin the filtering material is a stent.

44. The method of claim 39, wherein the filtering material is provided on first and second supporting structures.

45. The method of claim 44, wherein the first supporting structure is a source wire and the second supporting structure is a catheter.

46. The method of claim 39, wherein radiation is filtered by interposing a high density material between the source and the treatment site.

47. The method of claim 46, wherein radiation is filtered by interposing a material having a density of above about 20 grams per cubic centimeter between the source and the treatment site.

48. The method of claim 46, wherein radiation is filtered by interposing platinum between the source and the treatment site.

* * * * *